(12) United States Patent
Bradbury et al.

(10) Patent No.: US 7,902,365 B2
(45) Date of Patent: Mar. 8, 2011

(54) METHOD FOR SYNTHESIS OF 8-ALKOXY-9H-ISOTHIAZOLO[5,4-B] QUINOLINE-3,4-DIONES

(75) Inventors: Barton James Bradbury, Wallingford, CT (US); Jason Allan Wiles, Hamden, CT (US); Akihiro Hashimoto, Branford, CT (US); Qiuping Wang, Bethany, CT (US); Edlaine Lucien, New Haven, CT (US); Godwin Pais, Hamden, CT (US); Ha Young Kim, Cheshire, CT (US)

(73) Assignee: Achillion Pharmaceuticals, Inc., New Haven, CT (US)

( * ) Notice: Subject to any disclaimer, the term of this patent is extended or adjusted under 35 U.S.C. 154(b) by 672 days.

(21) Appl. No.: 11/840,006

(22) Filed: Aug. 16, 2007

(65) Prior Publication Data

US 2008/0071086 A1   Mar. 20, 2008

Related U.S. Application Data

(60) Provisional application No. 60/822,582, filed on Aug. 16, 2006.

(51) Int. Cl.
    *C07D 215/38* (2006.01)
(52) U.S. Cl. ......................... 546/155; 514/312
(58) Field of Classification Search ................. 546/155; 514/312
    See application file for complete search history.

(56) References Cited

U.S. PATENT DOCUMENTS 7,456,288 B2 *  11/2008  Rao et al. ............... 546/158

FOREIGN PATENT DOCUMENTS

| WO | 2005019228 A1 | 3/2005 |
| WO | 2006118605 A2 | 11/2006 |
| WO | 2007014308 A1 | 1/2007 |

OTHER PUBLICATIONS

Hashimoto, et al., "Practical Synthesis and Molecular Structure of a Potent Broad-Spectrum Antibacterial Isothiazoloquinolone," Organic Process Research & Development, 11: 389-398(2007).
International Search Report for Patent Application No. PCT/US2007/018251 dated Jan. 2, 2008.
Wang, et al., "Isothiazoloquinolones with Enhanced Antistaphylococcal Activiites against Multidrug-Resistant Strains: Effects of Structural Modifications at the 6-, 7-, and 8- Positions," J. Med. Chem., 50: 199-201 (2007).

* cited by examiner

*Primary Examiner* — D. Margaret Seaman
(74) *Attorney, Agent, or Firm* — Cantor Colburn LLP

(57) ABSTRACT

The present invention provides process for synthesis of 8-methoxy-9H-isothiazolo[5,4-b]quinoline-3,4-diones and 8A,9-dihydro-4aH-isothiazolo[5,4-b]quinoline-3,4-diones of the Formula A.

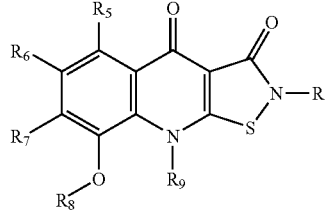

Formula A

The substituents R, $R_5$, $R_6$, $R_7$, $R_8$ and $R_9$ are defined herein. The invention also provides novel synthetic intermediates useful in the synthesis of 8-methoxy-9H-isothiazolo[5,4-b]quinoline-3,4-diones and 8A,9-dihydro-4aH-isothiazolo[5,4-b]quinoline-3,4-diones.

13 Claims, No Drawings

METHOD FOR SYNTHESIS OF 8-ALKOXY-9H-ISOTHIAZOLO[5,4-B] QUINOLINE-3,4-DIONES

CROSS REFERENCE TO RELATED APPLICATION

This application claims priority from U.S. Provisional Application No. 60/822,582 filed Jul. 16, 2006, which is hereby incorporated by reference in its entirety.

FIELD OF THE INVENTION

The present invention provides methods for synthesis of 8-alkoxy-9H-isothiazolo[5,4-b]quinoline-3,4-diones and 8A,9-dihydro-4aH-isothiazolo[5,4-b]quinoline-3,4-diones. The invention also provides synthetic intermediates useful in the synthesis of 8-alkoxy-9H-isothiazolo[5,4-b]quinoline-3,4-diones and 8A,9-dihydro-4aH-isothiazolo[5,4-b]quinoline-3,4-diones.

BACKGROUND OF THE INVENTION

Structural Formula A, shown below, and its tautomers represented by Formula B represent a class of potent antimicrobial compounds. Within Formula A and B the variables, e.g. R, $R_3$, and $R_5$ to $R_9$ carry the definitions that follow.

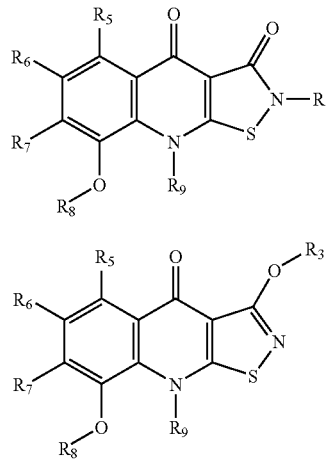

Formula A

Formula B

R is hydrogen, or R is $C_1$-$C_6$alkyl, $C_2$-$C_6$alkenyl, ($C_3$-$C_7$cycloalkyl)$C_0$-$C_4$alkyl, (aryl)$C_0$-$C_4$alkyl, or ($C_2$-$C_6$heterocycloalkyl)$C_0$-$C_2$alkyl, each of which is substituted with 0 to 5 substituents independently chosen from halogen, hydroxy, amino, cyano, nitro, $C_1$-$C_4$alkyl, $C_1$-$C_4$alkoxy, $C_1$-$C_2$haloalkyl, $C_1$-$C_2$haloalkoxy, mono- and di-$C_1$-$C_4$alkylamino, $C_2$-$C_4$alkanoyl, and $C_1$-$C_4$alkylthio.

$R_3$ is hydrogen, $C_1$-$C_6$alkyl, or $C_2$-$C_6$alkanoyl.

$R_5$ is hydrogen, hydroxy, amino, $C_1$-$C_2$alkyl, $C_1$-$C_2$alkoxy, mono- or di-($C_1$-$C_4$alkyl)amino, or mono-, di-, or tri-$C_1$-$C_4$alkylhydrazinyl.

$R_6$ is hydrogen, halogen, or amino.

$R_7$ is bromo or $R_7$ is a nitrogen-linked $C_1$-$C_4$alkylamino substituted with a 5 or 6-membered heteroaryl group having 1 or 2 heteroatoms independently chosen from N, O, and S, or substituted with a heterocycloalkyl group, which has 4 to 8 ring members, including 1 or 2 ring heteroatoms independently chosen from N, O, and S.

$R_7$ is a nitrogen-linked heterocycloalkyl or heterocycloalkenyl group, each of which has 4 to 8 ring members, including 0, 1, or 2 additional ring heteroatoms independently chosen from N, O, and S, forming part of a bicyclic system with a 3- to 8-membered cycloalkyl or heterocycloalkyl ring in fused or spiro orientation.

$R_7$ is a nitrogen-linked 6-membered heterocycloalkyl group, 0, 1, or 2 additional ring heteroatoms independently chosen from N, O, and S, and bridged with a methylene or ethylene bridge.

$R_7$ is a group of the formula

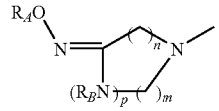

optionally attached to a $C_3$-$C_7$ spiro cycloalkyl or a spiro heterocycloalkyl.

$R_A$ is hydrogen, or $R_A$ is $C_1$-$C_8$alkyl, $C_2$-$C_6$alkenyl, $C_2$-$C_6$alkynyl, $C_2$-$C_6$alkanoyl, ($C_3$-$C_7$cycloalkyl)$C_0$-$C_4$alkyl, ($C_4$-$C_7$cycloalkenyl)$C_0$-$C_4$alkyl, (aryl)$C_0$-$C_4$alkyl, (aryl)(C=O)—, or ($C_2$-$C_6$heterocycloalkyl)$C_0$-$C_4$alkyl, each of which is substituted with 0 to 5 substituents independently chosen from halogen, hydroxy, amino, cyano, nitro, $C_1$-$C_4$alkyl, $C_1$-$C_4$alkoxy, $C_1$-$C_2$haloalkyl, $C_1$-$C_2$haloalkoxy, mono- and di-$C_1$-$C_4$alkylamino, $C_2$-$C_4$alkanoyl, and $C_1$-$C_4$alkylthio.

$R_B$ is hydrogen or $C_1$-$C_4$alkyl.

Each of which $R_7$ is substituted with 0 or 1 or more substituents independently chosen from (a) and 0, 1, or 2 substituents chosen from (b); wherein (a) is chosen from halogen, hydroxy, amino, nitro, $C_1$-$C_4$alkyl, $C_1$-$C_4$alkoxy, $C_1$-$C_2$haloalkyl, and $C_1$-$C_2$haloalkoxy, and (b) is oxo, cyano, hydroxy$C_1$-$C_4$alkyl, amino$C_1$-$C_4$alkyl, $C_1$-$C_6$alkylthio, $C_2$-$C_6$alkanoyl, (mono- or di-$C_1$-$C_4$alkyl)amino$C_0$-$C_4$alkyl, ($C_3$-$C_7$cycloalkyl)$C_0$-$C_4$alkyl, ($C_3$-$C_7$cycloalkyl)amino$C_0$-$C_4$alkyl, ($C_3$-$C_7$cycloalkyl)($C_1$-$C_4$alkyl)amino$C_0$-$C_4$alkyl, (heterocycloalkyl)$C_0$-$C_4$alkyl, (5-membered heteroaryl)$C_0$-$C_4$alkyl, or (aryl)$C_0$-$C_4$alkyl, where each of (b) other than oxo and cyano is substituted with 0 to 2 substituents independently chosen from halogen, hydroxy, amino, cyano, nitro, oxo, —COOH, —CONH$_2$, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy.

$R_8$ is $C_1$-$C_6$alkyl, $C_1$-$C_2$haloalkyl, or $C_3$-$C_7$cycloalkyl substituted with 0 or 1 or more halogen atoms.

$R_9$ is $C_1$-$C_4$alkyl, cyclopropyl, or phenyl, each of which is substituted with 0 to 3 substituents independently chosen from halogen, hydroxy, amino, $C_1$-$C_2$alkyl, $C_1$-$C_2$alkoxy, mono- and di-($C_1$-$C_2$)alkylamino, $C_1$-$C_2$haloalkyl, and $C_1$-$C_2$haloalkoxy.

The synthesis of these compounds has been described previously, in U.S. provisional patent application Ser. No. 11/494,205, filed Jul. 27, 2006, which is hereby incorporated by reference at pages 58 to 76, for its teachings regarding the synthesis of 8-alkoxy-9H-isothiazolo[5,4-b]quinoline-3,4-diones and in U.S. patent application Ser. No. 11/271,556 filed Nov. 10, 2005 which is hereby incorporated by reference at pages 43 to 51, for its teachings regarding the synthesis of 8A,9-dihydro-4aH-isothiazolo[5,4-b]quinoline-3,4-diones.

The previously described synthetic method produces significant amounts of impurities. Additionally the synthesis must be carried out, in part, in DMSO, a reactive and high-boiling solvent. The previously reported method requires chromatographic purification of an intermediate, while the procedure reported here does not require chromatographic purification. Additionally the previously reported method utilizes m-CPBA, a potentially explosive oxidant. Thus, a convenient and efficient synthesis that provides 8-alkoxy-9H-isothiazolo[5,4-b]quinoline-3,4-diones and 8A,9-dihydro-4aH-isothiazolo[5,4-b]quinoline-3,4-diones with reduced production of impurities and side products, and avoids the use of DMSO and m-CPBA is desirable. The present invention fulfills this need and provides additional advantages, which are described herein.

SUMMARY OF THE INVENTION

The present invention provides a process for making 8-alkoxy-9H-isothiazolo[5,4-b]quinoline-3,4-diones and 8A,9-dihydro-4aH-isothiazolo[5,4-b]quinoline-3,4-diones.

Thus in a first aspect the invention provides a method of making an 8-alkoxy-9H-isothiazolo[5,4-b]quinoline-3,4-dione, which method includes oxidizing a compound of Formula I with an oxidizing agent to make a sulfone compound of Formula II. Within Formula I and II X is fluoro, bromo, or chloro and $R_2$ and $R_4$ are independently chosen from $C_1$-$C_6$alkyl, $C_2$-$C_6$alkenyl, ($C_3$-$C_7$cycloalkyl)$C_0$-$C_4$alkyl, (aryl)$C_0$-$C_4$alkyl, and ($C_2$-$C_6$heterocycloalkyl)$C_0$-$C_2$alkyl, each of which is substituted with 0 to 5 substituents independently chosen from halogen, hydroxy, amino, cyano, nitro, $C_1$-$C_4$alkyl, $C_1$-$C_4$alkoxy, $C_1$-$C_2$haloalkyl, $C_1$-$C_2$haloalkoxy, mono- and di-$C_1$-$C_4$alkylamino, $C_2$-$C_4$alkanoyl, and $C_1$-$C_4$alkylthio. Within Formula I $R_{10}$ is —SH or —S$R_4$.

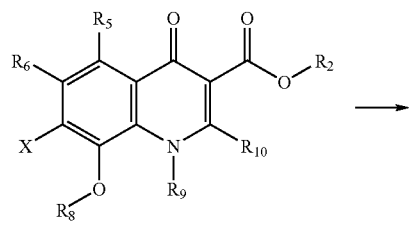

Formula I

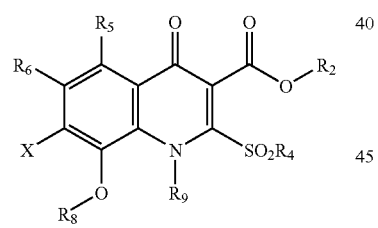

Formula II

The method also includes reacting a sulfone compound of Formula II with a cyclic secondary amine to form a compound of Formula III, in which $R_7$ represents an N-linked heterocycloalkyl substituent. The product of this step is then converted to a thiol compound with a conversion reagent.

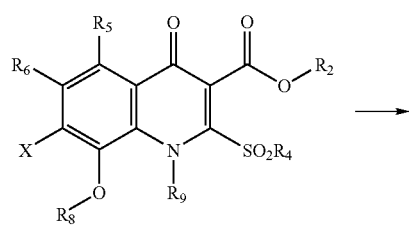

Formula II

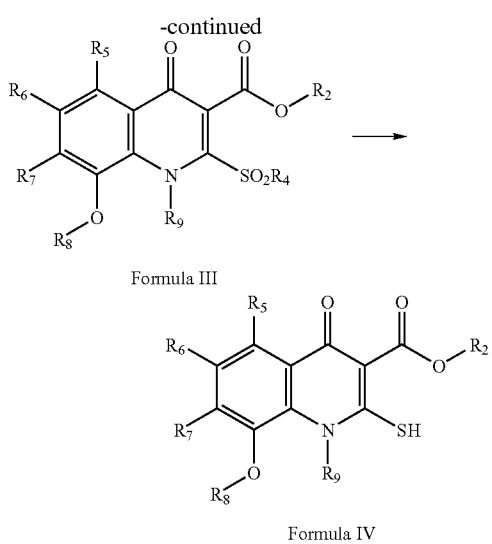

Formula III

Formula IV

The method includes cyclization of a compound of Formula IV to make an 8-alkoxy-9H-isothiazolo[5,4-b]quinoline-3,4-dione or 8A,9-dihydro-4aH-isothiazolo[5,4-b]quinoline-3,4-diones of Formula A. The cyclization may be effected by reacting a thiol compound of formula IV with hydroxylamine-O-sulfonic acid.

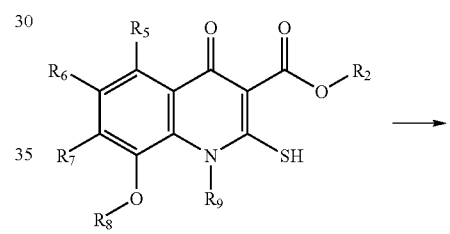

Formula IV

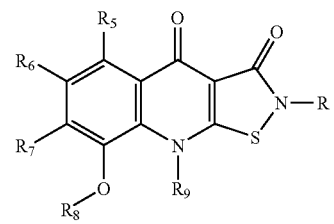

Formula A

The present invention provides synthetic intermediates useful for making 8-alkoxy-9H-isothiazolo[5,4-b]quinoline-3,4-diones and 8A,9-dihydro-4aH-isothiazolo[5,4-b]quinoline-3,4-diones. For example the invention provides synthetic intermediates of Formula I-Formula IV.

Within Formula I-Formula IV the variables X, $R_2$, $R_4$, $R_5$, $R_6$, $R_7$, $R_8$, and $R_9$ carry the definitions that follow.

X is chloro, bromo, fluoro; iodo, or triflate.

$R_2$ is $C_1$-$C_6$alkyl, $C_2$-$C_6$alkenyl, ($C_3$-$C_7$cycloalkyl)$C_0$-$C_4$alkyl, (aryl)$C_0$-$C_4$alkyl, or ($C_2$-$C_6$heterocycloalkyl)$C_0$-$C_2$alkyl, each of which is substituted with 0 to 5 substituents independently chosen from halogen, hydroxy, amino, cyano, nitro, $C_1$-$C_4$alkyl, $C_1$-$C_4$alkoxy, $C_1$-$C_2$haloalkyl, $C_1$-$C_2$haloalkoxy, mono- and di-$C_1$-$C_4$alkylamino, $C_2$-$C_4$alkanoyl, and $C_1$-$C_4$alkylthio.

$R_4$ is $C_1$-$C_6$alkyl, $C_2$-$C_6$alkenyl, ($C_3$-$C_7$cycloalkyl)$C_0$-$C_4$alkyl, (aryl)$C_0$-$C_4$alkyl, or ($C_2$-$C_6$heterocycloalkyl)$C_0$-

$C_2$alkyl, each of which is substituted with 0 to 5 substituents independently chosen from halogen, hydroxy, amino, cyano, nitro, $C_1$-$C_4$alkyl, $C_1$-$C_4$alkoxy, $C_1$-$C_2$haloalkyl, $C_1$-$C_2$haloalkoxy, mono- and di-$C_1$-$C_4$alkylamino, $C_2$-$C_4$alkanoyl, and $C_1$-$C_4$alkylthio.

$R_5$ is hydrogen, hydroxy, amino, $C_1$-$C_2$alkyl, $C_1$-$C_2$alkoxy, mono- or di-($C_1$-$C_4$alkyl)amino, or mono- or di-$C_1$-$C_4$alkylhydrazinyl.

$R_6$ is hydrogen, halogen, or amino.

$R_7$ is a nitrogen-linked heterocycloalkyl group, which has 4 to 8 ring members, including 0, 1, or 2 additional ring heteroatoms independently chosen from N, O, and S.

Or, $R_7$ is a nitrogen-linked $C_1$-$C_4$alkylamino substituted with a 5 or 6-membered heteroaryl group having 1 or 2 heteroatoms independently chosen from N, O, and S, or substituted with a heterocycloalkyl group, which has 4 to 8 ring members, including 1 or 2 ring heteroatoms independently chosen from N, O, and S.

Or, $R_7$ is a nitrogen-linked heterocycloalkyl or heterocycloalkenyl group, each of which has 4 to 8 ring members, including 0, 1, or 2 additional ring heteroatoms independently chosen from N, O, and S, forming part of a bicyclic system with a 3- to 8-membered cycloalkyl or heterocycloalkyl ring in fused or spiro orientation, Or, $R_7$ is a nitrogen-linked 6-membered heterocycloalkyl group, having 0, 1, or 2 additional ring heteroatoms independently chosen from N, O, and S, and bridged with a methylene or ethylene bridge.

Or, $R_7$ is a group of the formula

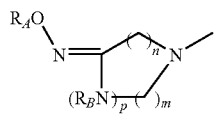

optionally attached to a $C_3$-$C_7$ spiro cycloalkyl or a spiro heterocycloalkyl.

$R_A$ is hydrogen, or $R_A$ is $C_1$-$C_8$alkyl, $C_2$-$C_6$alkenyl, $C_2$-$C_6$alkynyl, $C_2$-$C_6$alkanoyl, ($C_3$-$C_7$cycloalkyl)$C_0$-$C_4$alkyl, ($C_4$-$C_7$cycloalkenyl)$C_0$-$C_4$alkyl, (aryl)$C_0$-$C_4$alkyl, (aryl)(C=O)—, or ($C_2$-$C_6$heterocycloalkyl)$C_0$-$C_4$alkyl, each of which is substituted with 0 to 5 substituents independently chosen from halogen, hydroxy, amino, cyano, nitro, $C_1$-$C_4$alkyl, $C_1$-$C_4$alkoxy, $C_1$-$C_2$haloalkyl, $C_1$-$C_2$haloalkoxy, mono- and di-$C_1$-$C_4$alkylamino, $C_2$-$C_4$alkanoyl, and $C_1$-$C_4$alkylthio.

$R_B$ is hydrogen or $C_1$-$C_4$alkyl.

Each of which $R_7$ is substituted with 0 or 1 or more substituents independently chosen from (a) and 0, 1, or 2 substituents chosen from (b); wherein (a) is chosen from halogen, hydroxy, amino, nitro, $C_1$-$C_4$alkyl, $C_1$-$C_4$alkoxy, $C_1$-$C_2$haloalkyl, and $C_1$-$C_2$haloalkoxy, and (b) is oxo, cyano, hydroxy$C_1$-$C_4$alkyl, amino$C_1$-$C_4$alkyl, $C_1$-$C_6$alkylthio, $C_2$-$C_6$alkanoyl, (mono- or di-$C_1$-$C_4$alkyl)amino$C_0$-$C_4$alkyl, ($C_3$-$C_7$cycloalkyl)$C_0$-$C_4$alkyl, ($C_3$-$C_7$cycloalkyl)amino$C_0$-$C_4$alkyl, ($C_3$-$C_7$cycloalkyl)($C_1$-$C_4$alkyl)amino$C_0$-$C_4$alkyl, (heterocycloalkyl)$C_0$-$C_4$alkyl, (5-membered heteroaryl)$C_0$-$C_4$alkyl, or (aryl)$C_0$-$C_4$alkyl, where each of (b) other than oxo and cyano is substituted with 0 to 2 substituents independently chosen from halogen, hydroxy, amino, cyano, nitro, oxo, —COOH, —CONH$_2$, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy.

$R_8$ is $C_1$-$C_6$alkyl, $C_1$-$C_2$haloalkyl, or $C_3$-$C_7$cycloalkyl substituted with 0 or 1 or more halogen atoms.

$R_9$ is $C_1$-$C_4$alkyl, cyclopropyl, or phenyl, each of which is substituted with 0 to 3 substituents independently chosen from halogen, hydroxy, amino, $C_1$-$C_2$alkyl, $C_1$-$C_2$alkoxy, mono- and di-($C_1$-$C_2$)alkylamino, $C_1$-$C_2$haloalkyl, and $C_1$-$C_2$haloalkoxy.

DETAILED DESCRIPTION OF THE INVENTION

Chemical Description and Terminology

Prior to setting forth the invention in detail, it may be helpful to provide definitions of certain terms to be used herein. Compounds of the present invention are generally described using standard nomenclature.

In certain situations, the compounds described and claimed herein may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

Where a compound exists in various tautomeric forms, the invention is not limited to any one of the specific tautomers, but rather includes all tautomeric forms.

The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g. R, $R_1$ to $R_9$, and X. Unless otherwise specified, each variable within such a formula is defined independently of other variables. Thus, if a group is said to be substituted, e.g. with 0-2 R*, then said group may be substituted with up to two R* groups and R* at each occurrence is selected independently from the definition of R*.

The term "substituted," as used herein, means that any one or more hydrogen atoms on the designated atom or group is replaced with a selection from the indicated group, provided that the designated atom's normal valence is not exceeded. When a group is substituted by an "oxo" substituent a carbonyl bond replaces two hydrogen atoms on a carbon. An "oxo" substituent on an aromatic group or heteroaromatic group destroys the aromatic character of that group, e.g. a pyridyl substituted with oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified substituents are named into the core structure. For example, it is to be understood that when (cycloalkyl)alkyl is listed as a possible substituent the point of attachment of this substituent to the core structure is in the alkyl portion.

The exception to naming substituents into the ring is when the substituent is listed with a dash ("—") or double bond ("=") that is not between two letters or symbols. In that case the dash or double bond symbol is used to indicate a point of attachment for a substituent. For example, —$CONH_2$ is attached through the carbon atom.

As used herein, "alkyl" is intended to include both branched and straight-chain saturated aliphatic hydrocarbon groups, having the specified number of carbon atoms. Thus, the term $C_1$-$C_4$ alkyl as used herein includes alkyl groups having from 1 to about 4 carbon atoms. When $C_0$-$C_n$ alkyl is used herein in conjunction with another group, for example, (aryl)$C_0$-$C_4$ alkyl, the indicated group, in this case aryl, is either directly bound by a single covalent bond ($C_0$), or attached by an alkyl chain having the specified number of carbon atoms, in this case from 1 to about 4 carbon atoms. Examples of alkyl include, but are not limited to, methyl, ethyl, n-propyl, isopropyl, n-butyl, t-butyl, n-pentyl, and sec-pentyl.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. An "(alkoxy)alkyl group is an alkoxy group as defined herein attached through its oxygen atom to an alkyl bridge where the point of attachment to the substituted group is in the alkyl group.

"Alkanoyl" indicates an alkyl group as defined above, attached through a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3(C=O)$—.

As used herein, "mono- and/or di-alkylamino" indicate secondary or tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino. "mono- and/or di-(alkyl)aminoalkyl indicates a mono- and di-(alkyl)amino substituents as described herein attached to the group it substituted via a covalently bound alkyl linker having the indicated number of carbon atoms.

The term "mono-, di-, or tri-alkylhydrazinyl" indicates from 1 to 3 independently chosen alkyl groups as defined above attached through a single-bonded nitrogen-nitrogen linkage. At least one of the alkyl groups is attached to the terminal nitrogen (the nitrogen not bound to the core structure). When the term mono- or di-alkylhydrazinyl is used only the terminal nitrogen is alkyl substituted. Examples of alkylhydrazinyl groups include 2-butyl-1-hydrazinyl, 2-butyl-2-methyl-1-hydrazinyl, and 1,2-dimethyl-2-propyl-1-hydrazinyl.

The term "alkylthio" indicates an alkyl group as defined above attached through a sulfur linkage, i.e. a group of the formula alkyl-S—. Examples include ethylthio and pentylthio.

As used herein, the term "aminoalkyl" indicates an alkyl group as defined above substituted with at least one amino substituent. Similarly, the term "hydroxyalkyl" indicates an alkyl group as defined above, substituted with at least one hydroxyl substituent. In certain instances the alkyl group of the aminoalkyl or hydroxyalkyl group may be further substituted.

As used herein, the term "aryl" indicates aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl.

In the term "(aryl)alkyl", aryl and alkyl are as defined above, and the point of attachment is on the alkyl group. This term encompasses, but is not limited to, benzyl, phenylethyl, and piperonyl.

"Cycloalkyl" as used herein, indicates a saturated hydrocarbon ring group, having only carbon ring atoms and having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norborane or adamantane. In the term "(cycloalkyl)alkyl" the terms cycloalkyl, and alkyl are as defined above, and the point of attachment is on the alkyl. These terms include examples such as cyclopropylmethyl and cyclohexylmethyl.

"Haloalkyl" indicates both branched and straight-chain saturated aliphatic hydrocarbon groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge.

"Halo" or "halogen" as used herein refers to fluoro, chloro, bromo, or iodo.

The term "heterocycloalkyl" indicates a saturated monocyclic group containing from 1 to 3 heteroatoms independently chosen from N, O, and S, with remaining ring atoms being carbon or a saturated bicyclic group having at least one ring containing from 1 to 3 heteroatoms independently chosen from N, O, and S. Monocyclic heterocycloalkyl groups have from 3 to about 8 ring atoms, and more typically have from 5 to 7 ring atoms. Some preferred monocyclic heterocycloalkyl groups have 5 to 6 ring atoms and 1 or 2 heteroatoms chosen from N, O, and S. Bicyclic heterocycloalkyl groups have 2 saturated rings in fused or spiro orientation, with at least one ring having from 1 to 3 ring heteroatoms. Certain preferred bicyclic heterocycloalkyl groups have a 5- or 6-membered nitrogen containing ring in fused or spiro orientation with a $C_3$-$C_6$cycloalkyl group or a 4- to 6-membered heterocycloalkyl group containing 1 nitrogen atom.

Examples of heterocycloalkyl groups include morpholinyl, thiomorpholinyl, piperazinyl, piperidinyl, and pyrrolidinyl groups. In the term "heterocycloalkyl)alkyl" the terms heterocycloalkyl and alkyl are as defined above, and the point of attachment is on the alkyl.

Abbreviations

The following chemical abbreviations are used in Schemes 1 and 2 and Examples 1 to 3. Additional abbreviations used in these examples will be familiar to those of skill in the art of organic chemical synthesis.

| | |
|---|---|
| m-CPBA | meta-Chloroperoxybenzoic acid |
| DIEA | N,N-Diisopropylethyl amine |
| DME | Dimethyl ether |
| DMF | Dimethyl formamide |
| DMSO | Dimethylsulfoxide |
| EtOAc | Ethyl Acetate |
| MeOH | Methanol |
| PTFE | Polytetrafluoroethylene |
| UHP | Urea-hydrogen peroxide |
| THF | Tetrahydrofuran |

Chemical Synthesis

The previously described synthetic route proceeded via synthetic Scheme 1 in which the methyl sulfanyl starting material (1) was first oxidized to a sulfoxide (2) with the use of m-CPBA and then converted to a mercapto carboxylate (3) prior to cyclization to form the tricyclic 9-H-isothiazolo[5,4-b]quinoline-3,4-dione (4). The 9-H-isothiazolo[5,4-b]quinoline-3,4-dione (4) was then substituted at the 7-position with the appropriate amine to form the final 7-substituted-8-alkoxy-9-H-isothiazolo[5,4-b]quinoline-3,4-dione product (5).

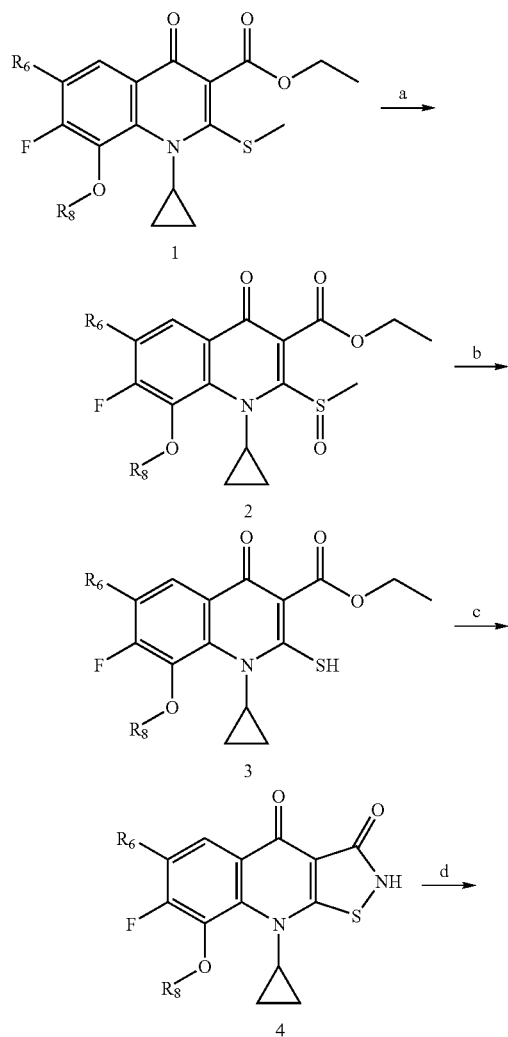

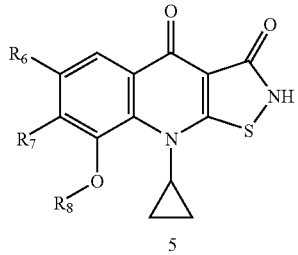

Within Scheme 1 the reagents and conditions are as follows: (a) 1 equiv m-CPBA, $CH_2Cl_2$, rt; (b) $NaSH \cdot xH_2O$, DMF, 50° C.; (c) $H_2NOSO_3H$, $NaHCO_3$, THF/water, rt; (d) (S)-1-methyl-1-pyrrolidin-3-yl-ethylamine, DMSO, ≧120° C. A significant amount of impurity A (up to ~35%) is observed in reaction (d) when 8-alkoxy-9H-isothiazolo[5,4-b]quionoline-3,4-diones or 8A,9-dihydro-4aH-isothiazolo[5,4-b]quinoline-3,4-diones are prepared using the method illustrated in Scheme 1. Within Scheme 1, and Scheme 2 below, $R_6$ is hydrogen, halogen, or amino and $R_8$ is $C_1C_6$alkyl, $C_1$-$C_2$haloalkyl, $C_3$-$C_7$cycloalkyl substituted with 0 or 1 or more halogen substituents. $R_7$ carries any of the definitions set forth herein for that variable.

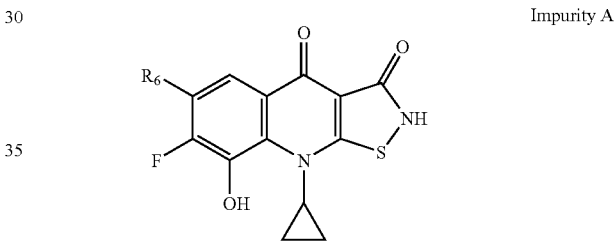

Impurity A

The inventors have discovered a novel synthetic route for preparing 7-substituted-8-alkoxy-9-H-isothiazolo[5,4-b]quinoline-3,4-diones and 8A,9-dihydro-4aH-isothiazolo[5,4-b]quinoline-3,4-diones. An overview of this method is provided in synthetic scheme 2. In this method the methyl sulfanyl starting material (1) is oxidized to a sulfone intermediate (6). Within Scheme 2 the reagents and conditions are as follows: (e) excess OXONE (DuPont Specialty Chemicals, active ingredient is potassium peroxymonosulfate CAS RN 10058-23-8), MeOH/water, 55-60° C.; (f) (R)-1-methyl-1-pyrrolidin-3-yl-ethylamine, DMF, 70° C.; (g) $NaSH \cdot xH_2O$, DME/water, rt; and (h) $H_2NOSO_3H$, $K_2CO_3$, DME/water, rt.

Scheme 2

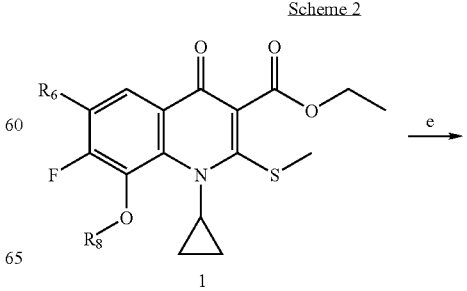

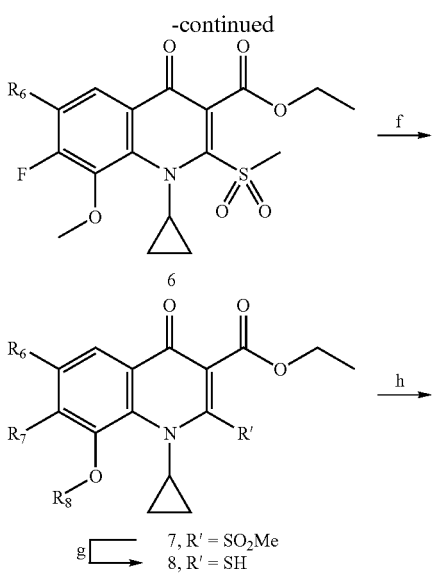

6

7, R' = SO₂Me
8, R' = SH

5

The process illustrated by Scheme 2 presents several advantages over the previously used process illustrated by Scheme 1. Preparation of the sulfone intermediate (6) avoids the use of m-CPBA, which is potentially explosive. The process illustrated by Scheme 2 also eliminates the need for stoichiometric control of the oxidant. OXONE, the oxidant used in step (e) of Scheme 2, may simply be used in excess. The need for chromatographic purification of sulfoxide (2) is eliminated as the sulfone (6) crystallizes easily from the reaction mixture. Impurity B is observed in reaction (f), but the amount (up to 20%) is less than the amount of impurity A observed in reaction (d). Impurity B is removed easily by recrystallization from ethyl acetate. In contrast impurity A in Scheme 1 must be removed using preparative HPLC, a more difficult process. Chromatographic purification of the sulfone (6) is not necessary, however, purification of the sulfoxide (2) is necessary.

Impurity B

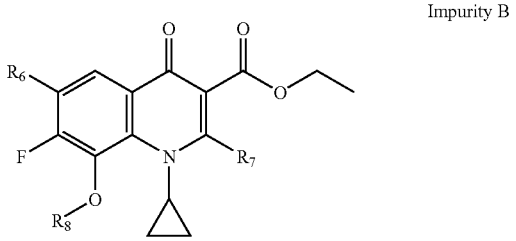

Additionally, conversion of (7) to (8) is faster than conversion of (2) to (3) (displacement of the sulfone is more rapid than displacement of the sulfoxide). Reaction (f) (conversion of (6) to (7)) employs more convenient synthetic conditions than reaction (d) (conversion of (4) to (5)). For example, reaction (f) is conducted at lower temperatures and eliminates use of DMSO (a reactive and high-boiling solvent). This reaction produces lower levels of impurities and side products than the reaction of Scheme 1.

The invention provides a process for making anti-microbial compounds of Formula A and also provides methods for making synthetic intermediates useful in the synthesis of compounds of Formula A.

In one aspect the invention includes a method of making a sulfone intermediate of Formula II comprising oxidizing a compound of Formula I in which X is fluoro or chloro, preferably fluoro, with an oxidizing agent. This reaction appears in Scheme 2 as reaction (e). In this aspect of the invention the oxidizing agent may be potassium monoperoxysulfate (such as OXONE). Other suitable oxidizing agents include urea hydrogen peroxide (in formic acid) and sodium periodate. Reaction (e) may be run at a temperature of 20° C. to 70° C. Reaction (e) may be run in an aqueous/alcohol (e.g., water/methanol and water/ethanol) solvent system or may be run in any of the following solvents: acetonitrile, dimethylformamide (DMF), or N-methylpyrrolidone (NMP).

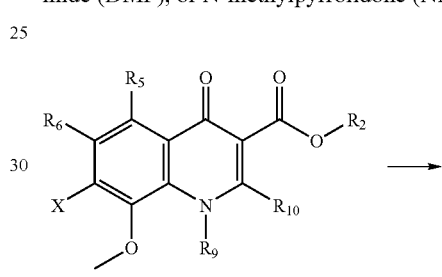

Formula I

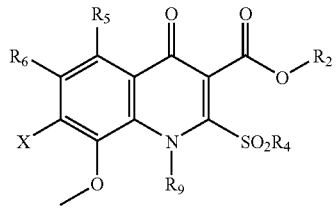

Formula II

In another aspect the invention includes a method of reacting a sulfone compound of Formula II with a cyclic secondary amine to form a compound of Formula III, in which $R_7$ represents an N-linked heterocycloalkyl substituent (Reaction (f) in Scheme 2). The product of this step is then converted to a thiol compound with a conversion reagent (Reaction (g) in Scheme 2).

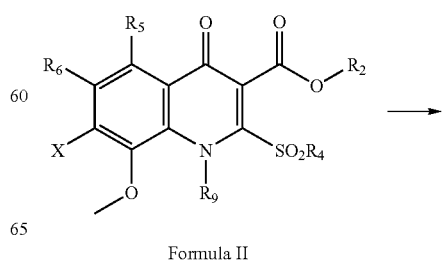

Formula II

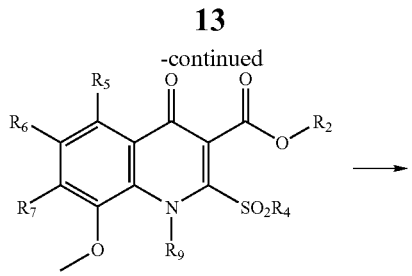

Formula III

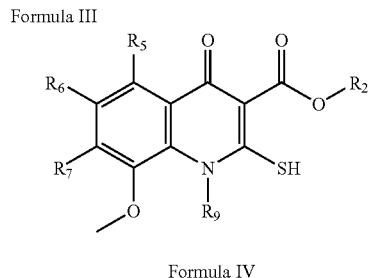

Formula IV

In some embodiments reaction (f) is performed under dry conditions in a polar solvent. For example, the solvent may be DMF. Other suitable solvents include dimethylacetamide (DMA), N-methylpyrrolidone (NMP), 1,2-dimethoxyethane (DME), and tetrahydrofuran (THF).

The secondary amine (which will become the $R_7$ substituent) used in reaction (f) may be pyrrolidine, piperidine, piperazine, morpholine, thiomorpholine, or azepane substituted with 0 to 2 substituents independently chosen from one or more of (a) and 0 or 1 substituents (b). Wherein (a) is chosen from halogen, hydroxy, amino, nitro, $C_1$-$C_4$alkyl, $C_1$-$C_4$alkoxy, $C_1$-$C_2$haloalkyl, and $C_1$-$C_2$haloalkoxy, and (b) is oxo, amino, cyano, hydroxy$C_1$-$C_4$allyl, amino$C_1$-$C_4$alkyl, $C_1$-$C_6$alkylthio, $C_2$-$C_6$alkanoyl, (mono- or di-$C_1$-$C_4$alkyl)amino$C_0$-$C_4$alkyl, ($C_3$-$C_7$cycloalkyl)$C_0$-$C_4$alkyl, ($C_3$-$C_7$cycloalkyl)amino$C_0$-$C_4$alkyl, ($C_3$-$C_7$cycloalkyl)($C_1$-$C_4$alkyl)amino$C_0$-$C_4$alkyl, (heterocycloalkyl)$C_0$-$C_4$alkyl, or (aryl)$C_0$-$C_4$alkyl, where each of (b) other than oxo and cyano is substituted with 0 to 2 substituents independently chosen from halogen, hydroxy, amino, cyano, nitro, oxo, —COOH, —CONH$_2$, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy.

In some embodiments it is desirable to conduct the reaction in the presence of an additional amine, such as DIEA.

In some embodiments the secondary amine used in reaction (f) is pyrrolidine, which is substituted with 0 to 2 substituents independently chosen from one or more of (a) and 0, 1, or 2 substituents (b).

In some embodiments the secondary amine used in reaction (f) is pyrrolidine substituted with (5-membered heteroaryl)$C_0$-$C_4$alkyl, which is substituted with 0 to 2 independently chosen from 0 to 2 substituents independently chosen from halogen, hydroxy, amino, cyano, nitro, oxo, —COOH, —CONH$_2$, $C_1$-$C_4$alkyl, $C_2$-$C_4$alkenyl, $C_2$-$C_4$alkynyl, $C_1$-$C_4$alkoxy, mono- and di-($C_1$-$C_4$alkyl)amino, $C_1$-$C_2$haloalkyl, and $C_1$-$C_2$haloalkoxy. Exemplary 5-membered heteroaryl group includes imidazolyl, thiazolyl, furanyl, oxazolyl, thienyl, pyrrolyl, pyrazolyl, triazolyl, tetrazolyl, or oxadiazolyl group.

In some embodiments the secondary amine is a thiazolylmethyl group substituted with amino or an imidazolyl methyl group substituted with amino, e.g. the secondary amine may be

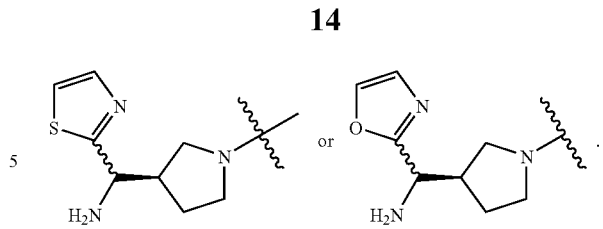

In some embodiments the secondary amine used in reaction (f) is pyrrolidine substituted with one group (b) and optionally substituted with 1 methyl or halogen substituent wherein (b) is oxo, amino, cyano, hydroxy$C_1$-$C_4$alkyl, amino$C_1$-$C_4$alkyl, $C_2$-$C_4$alkanoyl, (mono- or di-$C_1$-$C_4$alkyl)amino$C_0$-$C_4$alkyl, ($C_3$-$C_7$cycloalkyl)$C_0$-$C_2$alkyl substituted with amino, ($C_3$-$C_7$cycloalkylamino)$C_0$-$C_4$alkyl, or ($C_3$-$C_7$cycloalkyl)($C_1$-$C_4$alkyl)amino$C_0$-$C_4$alkyl.

In some embodiments the secondary amine used in reaction (f) is an amine of the formula

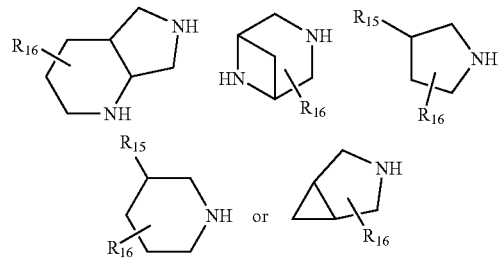

in which $R_{15}$ is (b); and $R_{16}$ is 0 or 1 or more substituents chosen from amino, hydroxy, chloro, fluoro, methyl, methoxy, trifluoromethyl, and trifluoromethoxy.

In some embodiments the secondary amine used in reaction (f) is

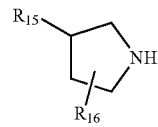

in which $R_{15}$ is (b); and $R_{16}$ is 0 or 1 or more substituents chosen from amino, hydroxy, chloro, fluoro, methyl, methoxy, trifluoromethyl, and trifluoromethoxy.

$R_{15}$ may also carry the following definition: oxo, amino, cyano, hydroxy$C_1$-$C_4$alkyl, amino$C_1$-$C_4$alkyl, $C_2$-$C_4$alkanoyl, (mono- or di-$C_1$-$C_4$alkylamino)$C_0$-$C_4$alkyl, ($C_3$-$C_7$cycloalkyl)$C_0$-$C_2$alkyl substituted with amino, ($C_3$-$C_7$cycloalkylamino)$C_0$-$C_4$alkyl, or ($C_3$-$C_7$cycloalkyl)($C_1$-$C_4$alkyl)amino$C_0$-$C_4$alkyl. In certain embodiments of $R_{15}$ is oxo, cyano, hydroxy$C_1$-$C_4$alkyl, amino$C_1$-$C_4$alkyl, acetyl, (mono- or di-$C_1$-$C_2$alkylamino)$C_1$-$C_4$alkyl, cyclopropyl substituted with amino, or ($C_3$-$C_7$cycloalkylamino)$C_0$-$C_4$alkyl; and $R_{16}$ is 0 or 1 substituent chosen from hydroxy, amino, chloro, and methyl.

In some embodiments the secondary amine used in reaction (f) is 1-(pyrrolidin-3-yl)cyclopropanamine; 2-(pyrrolidin-3-yl)propan-2-amine; N-((4-methylpyrrolidin-3-yl)methyl)cyclopropanamine; 1-(pyrrolidin-3-yl)ethanamine; N-methyl-1-(pyrrolidin-3-yl)ethanamine; N-methyl-2-(pyrrolidin-3-yl)propan-2-amine; N,N-dimethylpyrrolidin-3-amine; N-methylpyrrolidin-3-amine; N-methyl-1-(pyrrolidin-3-yl)methanamine; pyrrolidin-3-ylmethanamine;

4-methylpyrrolidine-3-carbonitrile; N-ethyl-1-(pyrrolidin-3-yl)ethanamine; N-ethyl-2-(pyrrolidin-3-yl)propan-2-amine; pyrrolidin-3-amine; (3-methylpyrrolidin-3-yl)methanol; N,N-dimethyl-1-(pyrrolidin-3-yl)ethanamine; N,N-dimethyl-2-(pyrrolidin-3-yl)propan-2-amine; N,N-dimethyl-1-(pyrrolidin-3-yl)methanamine; N-methyl-1-(pyrrolidin-3-yl)propan-1-amine; N-methyl-1-(pyrrolidin-3-yl)propan-1-amine; N-(1-(pyrrolidin-3-yl)ethyl)cyclopropanamine; or N-(1-(pyrrolidin-3-yl)ethyl)cyclopentanamine.

In some embodiments the secondary amine used in reaction (f) is a 5- or 6-membered nitrogen-linked heterocycloalkyl, which has 0 or 1 additional nitrogen atoms, which 5- or 6-membered nitrogen-linked heterocycloalkyl is part of a bicyclic ring system having a fused $C_3$-$C_6$cycloalkyl or a fused 4- to 6-membered heterocycloalkyl containing 1 nitrogen atom, which bicyclic ring system is substituted with 0, 1, or 2 substituents independently chosen from independently chosen from halogen, hydroxy, amino, oxo, cyano, $C_1$-$C_2$alkyl, $C_1$-$C_2$alkoxy, $C_1$-$C_2$haloalkyl, and $C_1$-$C_2$haloalkoxy.

In some embodiments the secondary amine used in reaction (f) is a 5- or 6-membered nitrogen-linked heterocycloalkyl which is part of a bicyclic ring system is a pyrrolidinyl or piperidinyl and is fused to a $C_3$-$C_6$cycloalkyl, pyrrolidinyl, or piperidinyl which bicyclic ring is substituted with 0, 1, or 2 substituents independently chosen from halogen, methyl, and methoxy.

The conversion reagent used in reaction (g) may be $NaSH.xH_2O$, anhydrous sodium hydrosulfite ($NaSH.xH_2O$ where x=0). Other suitable conversion reagents include $Na_2S$ or $Na_2S.9H_2O$. Reaction (g) may be conducted at room temperature or at any temperature from 0° C. to 50° C. In certain embodiments reaction (g) is conducted in a polar solvent such as DMF. Other suitable solvents include DME/water, THF/water, EtOH/water. Oxygen should be excluded from the reaction mixture when conducting reaction (g). Reaction (g) may be conducted in an inert gas atmosphere, for example under Argon, $N_2$, or He.

The invention includes a method of cyclization of a compound of Formula IV to prepare an 8-alkoxy-9H-isothiazolo[5,4-b]quinoline-3,4-dione of Formula A (reaction (h)).

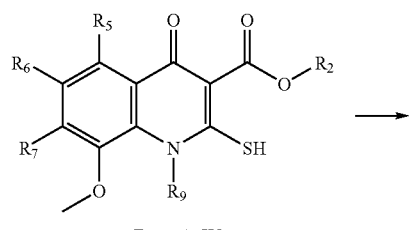

Formula IV

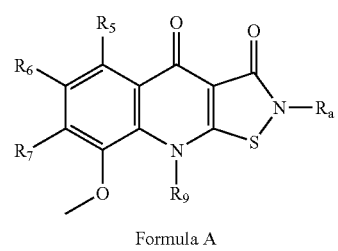

Formula A

The cyclization may be effected by reacting a thiol compound of formula IV with hydroxylamine-O-sulfonic acid. Other suitable reagents for effecting the cyclization include hydroxylamine compounds such as O-mesitylenesulfonylhydroxylamine and O-nitrophenylhydroxylamine. The cyclization reaction (h) may be conducted in a polar solvent such as THF/water. Other suitable solvents include DME/water and DMF/water. The cyclization reaction (h) can be conducted at basic pH. In certain embodiments the cyclization is conducted at pH 9-10. In certain embodiments the basic pH is supplied by adding $K_3PO_4$ or $NaHCO_3$. Other suitable bases include $K_2CO_3$ and $Et_3N$.

Chemical Description

In addition to the definitions set forth in the Summary of Invention section for the groups $R_5$, $R_6$, $R_7$, and $R_9$ these groups may also carry any of the following definitions.

The $R_2$ and $R_4$ groups $R_2$ is $C_1$-$C_6$alkyl, or in some embodiments $R_2$ is $C_1$-$C_4$alkyl.

$R_4$ is $C_1$-$C_6$alkyl, or in some embodiments $R_4$ is $C_1$-$C_4$alkyl.

The $R_5$ group i. $R_5$ is hydrogen

The $R_6$ group i. $R_6$ is fluoro or hydrogen.

ii. $R_6$ is fluoro.

The $R_7$ group i. $R_7$ is a nitrogen-linked heterocycloalkyl group, which has 4 to 8 ring members, including 0, 1, or 2 additional ring heteroatoms independently chosen from N, O, and S, which is substituted with 0 or 1 or more substituents independently chosen from (a) and 0, 1, or 2 substituents chosen from (b).

ii. $R_7$ is a pyrrolidinyl, piperidinyl, piperazinyl, morpholinyl, thiomorpholinyl, or azepanyl group substituted with with 0 to 2 substituents independently chosen from or more of (a) and 0 or 1 substituents (b).

iii. $R_7$ is a pyrrolidinyl group, which is substituted with 0 to 2 substituents independently chosen from one or more of (a) and 0 or 1 substituents (b).

iv. $R_7$ is pyrrolidinyl group substituted with one group (b) and optionally substituted with 1 methyl or halogen substituent wherein (b) is oxo, amino, cyano, hydroxy$C_1$-$C_4$alkyl, amino$C_1$-$C_4$alkyl, $C_2$-$C_4$alkanoyl, (mono- or di-$C_1$-$C_4$alkyl)amino$C_0$-$C_4$alkyl, ($C_3$-$C_7$cycloalkyl)$C_0$-$C_2$alkyl substituted with amino, ($C_3$-$C_7$cycloalkylamino)$C_0$-$C_4$alkyl, or ($C_3$-$C_7$cycloalkyl)($C_1$-$C_4$alkyl)amino$C_0$-$C_4$alkyl; each of which is substituted with 0 to 2 $C_1$-$C_4$alkyl.

v. $R_7$ is a group of formula

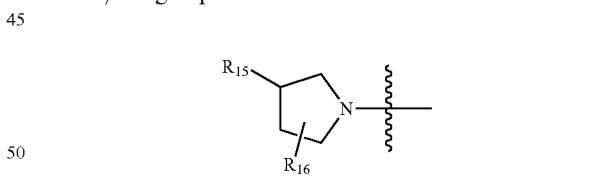

in which $R_{15}$ is (b); and $R_{16}$ is 0 or 1 or more substituents chosen from amino, hydroxy, chloro, fluoro, methyl, methoxy, trifluoromethyl, and trifluoromethoxy.

vi. In some embodiments $R_{15}$ is oxo, amino, cyano, hydroxy$C_1$-$C_4$alkyl, amino$C_1$-$C_4$alkyl, $C_2$-$C_4$alkanoyl, (mono- or di-$C_1$-$C_4$alkylamino)$C_0$-$C_4$alkyl, ($C_3$-$C_7$cycloalkyl)$C_0$-$C_2$alkyl substituted with amino, ($C_3$-$C_7$cycloalkylamino)$C_0$-$C_4$alkyl, or ($C_3$-$C_7$cycloalkyl)($C_1$-$C_4$alkyl)amino$C_0$-$C_4$alkyl.

vii. In certain embodiments $R_{15}$ is oxo, cyano, hydroxy$C_1$-$C_4$alkyl, amino$C_1$-$C_4$alkyl, acetyl, (mono- or di-$C_1$-$C_2$alkylamino)$C_1$-$C_4$alkyl, cyclopropyl substituted with amino, or ($C_3$-$C_7$cycloalkylamino)$C_0$-$C_4$alkyl; and $R_{16}$ is 0 or 1 substituent chosen from hydroxy, amino, chloro, and methyl.

viii. In other embodiments $R_{15}$ is hydroxy$C_1$-$C_4$alkyl, amino$C_1$-$C_4$alkyl, $C_2$-$C_4$alkanoyl, (mono- or di-$C_1$-$C_4$alkylamino)$C_0$-$C_4$alkyl, ($C_3$-$C_7$cycloalkyl)$C_0$-$C_2$alkyl substituted with amino, ($C_3$-$C_7$cycloalkylamino)$C_0$-$C_4$alkyl, or ($C_3$-$C_7$cycloalkyl)($C_1$-$C_4$alkyl)amino$C_0$-$C_4$alkyl; each of which is substituted with 0 to 2 $C_1$-$C_4$alkyl.

ix. In certain embodiments $R_7$ is a group of formula

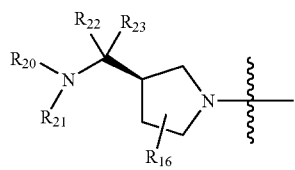

in which $R_{16}$ is 0 or 1 or more substituents chosen from amino, hydroxy, chloro, fluoro, methyl, methoxy, trifluoromethyl, and trifluoromethoxy; $R_{20}$ and $R_{21}$ are independently hydrogen or $C_1$-$C_4$alkyl; and $R_{22}$ and $R_{23}$ are independently hydrogen, $C_1$-$C_4$alkyl or $R_{22}$ and $R_{23}$ may be joined to form a cyclopropyl or cyclobutyl ring.

x. $R_7$ is

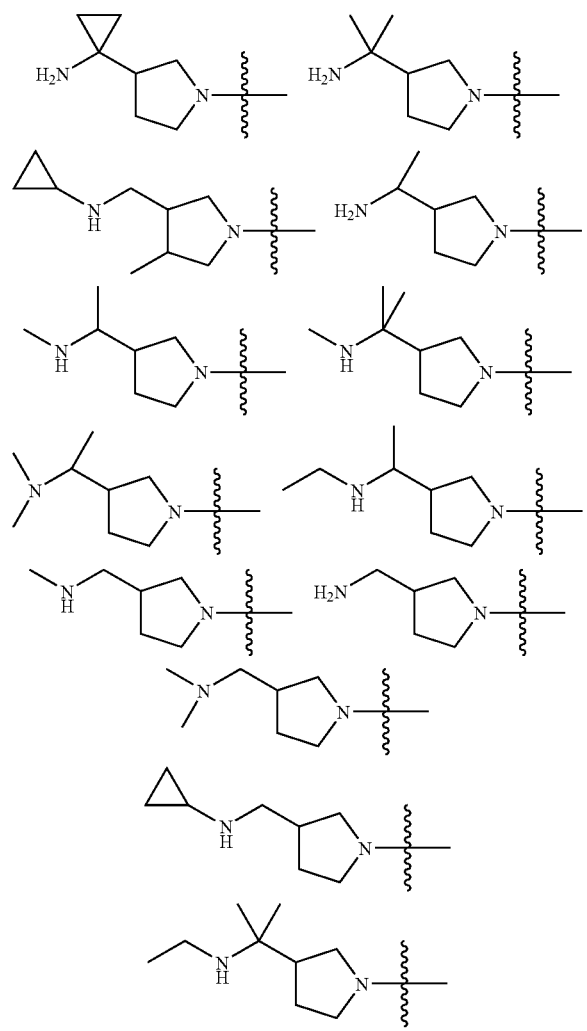

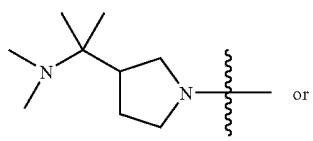

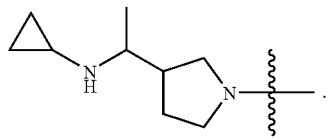

xii. $R_7$ is a 5- or 6-membered nitrogen-linked heterocycloalkyl, which has 0 or 1 additional nitrogen atoms, which 5- or 6-membered nitrogen-linked heterocycloalkyl is part of a bicyclic ring system having a fused $C_3$-$C_6$cycloalkyl or a fused 4- to 6-membered heterocycloalkyl containing 1 nitrogen atom, which bicyclic ring system is substituted with 0, 1, or 2 substituents independently chosen from independently chosen from halogen, hydroxy, amino, oxo, cyano, $C_1$-$C_2$alkyl, $C_1$-$C_2$alkoxy, $C_1$-$C_2$haloalkyl, and $C_1$-$C_2$haloalkoxy.

xiii. In some embodiments the 5- or 6-membered nitrogen-linked heterocycloalkyl which is part of a bicyclic ring system is a pyrrolidinyl or piperidinyl and is fused to a $C_3$-$C_6$cycloalkyl, pyrrolidinyl, or piperidinyl which bicyclic ring is substituted with 0, 1, or 2 substituents independently chosen from halogen, methyl, and methoxy.

xiv. $R_7$ is a pyrrolidinyl group substituted with (5-membered heteroaryl)$C_0$-$C_4$alkyl, which is substituted with 0 to 3 independently chosen from 0 to 3 substituents independently chosen from halogen, hydroxy, amino, cyano, nitro, oxo, —COOH, —CONH$_2$, $C_1$-$C_4$alkyl, $C_2$-$C_4$alkenyl, $C_2$-$C_4$alkynyl, $C_1$-$C_4$alkoxy, mono- and di-($C_1$-$C_4$alkyl)amino, $C_1$-$C_2$haloalkyl, and $C_1$-$C_2$haloalkoxy. The 5-membered heteroaryl group is an imidazolyl, thiazolyl, furanyl, oxazolyl, thienyl, pyrazolyl, triazolyl, tetrazolyl, or oxadiazolyl group in some embodiments.

xv. $R_7$ is a nitrogen-linked $C_1$-$C_4$alkylamino substituted with a 5 or 6-membered heteroaryl group having 1 or 2 heteroatoms independently chosen from N, O, and S, or substituted with a heterocycloalkyl group, which has 4 to 8 ring members, including 1 or 2 ring heteroatoms independently chosen from N, O, and S; which is substituted with 0 or 1 or more substituents independently chosen from (a) and 0, 1, or 2 substituents chosen from (b).

xvi. $R_7$ is $C_1$-$C_4$alkylamino substituted with a pyridyl, pyrimidinyl, piperazinyl, piperidinyl, or morpholinyl, each of which is substituted with 0, 1, or 2 substituents independently chosen from halogen, hydroxy, amino, oxo, cyano, $C_1$-$C_2$alkyl, $C_1$-$C_2$alkoxy, $C_1$-$C_2$haloalkyl, and $C_1$-$C_2$haloalkoxy.

xvii. $R_7$ is $C_1$-$C_2$alkylamino substituted with pyridyl, piperazinyl, piperidinyl, or morpholinyl, each of which is substituted with 0, 1, or 2 substituents independently chosen from halogen, methyl, and methoxy.

xviii. $R_7$ is a thiazolylmethyl group substituted with amino or an imidazolyl methyl group substituted with amino.

xix. R_7 is

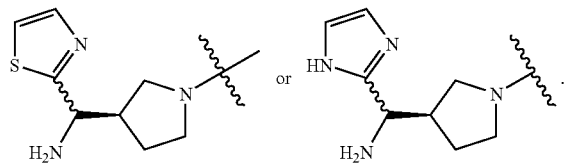

or.

xx. $R_7$ is a nitrogen-linked heterocycloalkyl or heterocycloalkenyl group, each of which has 4 to 8 ring members, including 0, 1, or 2 additional ring heteroatoms independently chosen from N, O, and S, forming part of a bicyclic system with a 3- to 8-membered cycloalkyl or heterocycloalkyl ring in fused or spiro orientation, each of which $R_7$ is substituted with 0 or 1 or more substituents independently chosen from (a) and 0 or 1 substituents chosen from (b).

xxi. $R_7$ is a piperidinyl, piperazinyl, or pyrrolidinyl group, which is part of a bicyclic system having a spiro attached $C_3$-$C_4$cycloalkyl, dioxolanyl, or azetidinyl group, which bicyclic system is substituted with 0, 1, or 2 substituents independently chosen from halogen, hydroxy, amino, oxo, cyano, $C_1$-$C_2$alkyl, $C_1$-$C_2$alkoxy, $C_1$-$C_2$haloalkyl, and $C_1$-$C_2$haloalkoxy. $R_7$ is a 5- or 6-membered nitrogen-linked heterocycloalkyl, which has 0 or 1 additional nitrogen atoms, which 5- or 6-membered nitrogen-linked heterocycloalkyl is part of a bicyclic ring system having a fused $C_3$-$C_6$cycloalkyl or a fused 4- to 6-membered heterocycloalkyl containing 1 nitrogen atom, which bicyclic ring system is substituted with 0, 1, or 2 substituents independently chosen from independently chosen from halogen, hydroxy, amino, oxo, cyano, $C_1$-$C_2$alkyl, $C_1$-$C_2$alkoxy, $C_1$-$C_2$haloalkyl, and $C_1$-$C_2$haloalkoxy.

xxii. In certain embodiments the 5- or 6-membered nitrogen-linked heterocycloalkyl which is part of a bicyclic ring system is a pyrrolidinyl or piperidinyl and is fused to a C3-C6cycloalkyl, pyrrolidinyl, or piperidinyl which bicyclic ring is substituted with 0, 1, or 2 substituents independently chosen from halogen, methyl, and methoxy.

xxiii. $R_7$ is a group of the formula

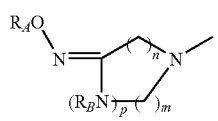

optionally attached to a $C_3$-$C_7$ spiro cycloalkyl or a spiro heterocycloalkyl.

xxiv. $R_7$ is substituted with 0, 1, or 2 substituents independently chosen from $C_1$-$C_4$alkyl, $C_1$-$C_4$alkoxy, hydroxy$C_1$-$C_4$alkyl, amino$C_1$-$C_4$alkyl, and $C_3$-$C_7$cycloalkyl substituted with amino.

xxv. $R_7$ is a group of the formula shown in xxiii, substituted with 0, 1, or 2 substituents independently chosen from $C_1$-$C_4$alkyl, $C_1$-$C_4$alkoxy, hydroxy$C_1$-$C_4$alkyl, amino$C_1$-$C_4$alkyl, and $C_3$-$C_7$cycloalkyl substituted with amino; and $R_A$ is hydrogen, $C_1$-$C_2$alkyl, or benzyl.

xxvi. $R_7$ is a group of the formula

The $R_8$ and $R_9$ groups
 i. $R_8$ is $C_1$-$C_6$alkyl.
 ii $R_8$ is $C_1$-$C_4$alkyl.
 iii. $R_8$ is difluoromethyl or fluorocyclopropyl.
 iv. $R_8$ is hydrogen.
 v. $R_9$ is $C_1$-$C_4$alkyl or cyclopropyl, or $R_9$ is phenyl substituted with 2 substituents chosen from halogen, hydroxy, amino, $C_1$-$C_2$alkyl, $C_1$-$C_2$alkoxy, mono- and di-($C_1$-$C_2$)alkylamino, $C_1$-$C_2$haloalkyl, and $C_1$-$C_2$haloalkoxy.
 vi. $R_9$ is cyclopropyl.

vii. Any of the above definitions for the variables $R_5$ to $R_7$ and $R_9$ may be combined to form an intermediate of Formula I to IV so long as a useful intermediate results. A useful intermediate is an intermediate that is sufficiently stable to be used in one of reactions (e) to (h) shown in Scheme 2.

EXAMPLES

General Methods

All nonaqueous reactions are performed under an atmosphere of dry argon gas (99.99%). NMR spectra are recorded at ambient temperature using a Bruker Avance 300 spectrometer ($^1$H at 300.1 MHz and $^{13}$C at 75.5 MHz,). The chemical shifts for $^1$H and $^{13}$C are reported in parts per million (δ) relative to external tetramethylsilane and are referenced to signals of residual protons in the deuterated solvent. Analytical HPLC is performed using a Waters X-bridge C18 150×4.6 mm 3.5 μm column with a 20-min linear gradient elution of increasing concentrations of acetonitrile in water (5 to 95%) containing 0.1% trifluoroacetic acid with a flow rate of 1.0 mL/min and WV detection at 254 nm. Low-resolution mass spectra are recorded on a Thermo Finnigan Surveyor MSQ instrument (operating in APCI mode) equipped with a Gilson liquid chromatograph. Unless noted otherwise, the quasi-molecular ions, [M+H]$^+$, observed in the low-resolution mass spectra are the base peaks. Melting points are recorded on an Electrothermal Model IA9100 digital melting point apparatus.

The skilled artisan will readily appreciate that certain reactions are best carried out when other functionalities are masked or protected in the compound, thus increasing the yield of the reaction and/or avoiding any undesirable side reactions. Often, the skilled artisan utilizes protecting groups to accomplish such increased yields or to avoid the undesired reactions. These reactions are found in the literature and are also well within the scope of the skilled artisan.

This invention is further illustrated by the following examples that should not be construed as limiting. The contents of all references, patents and published patent applications cited throughout this application are incorporated herein by reference.

Example 1

SYNTHESIS OF (R)-7-[3-(1-AMINO-1-METHYL-ETHYL)PYRROLIDIN-1-YL]-9-CYCLOPROPYL-6-FLUORO-8-METHOXY-9H-ISOTHIAZOLO[5,4-B]QUNIOLINE-3,4-DIONE (5)

Step 1. Ethyl 1-cyclopropyl-6,7-difluoro-2-methanesulfonyl-8-methoxy-4-oxo-1,4-dihydroquinoline-3-carboxylate (6)

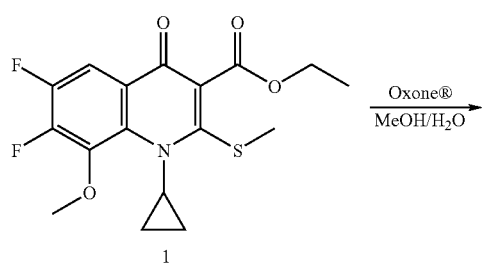

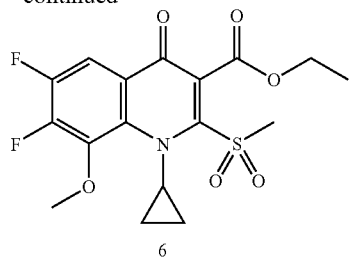

Water (180 mL), followed by Oxone® (Dupont Specialty Chemicals) (170 g, 277 mmol), is added to a suspension of 1 in MeOH (510 mL). The reaction mixture is heated with stirring at 55-60° C. for 3 h. The reaction mixture is cooled to room temperature, diluted with water (40 mL), and stirred at 5° C. (ice bath) for 30 min. The resulting crystals are collected by filtration, washed with water (2×100 mL), and dried to afford 6 (13.8 g). This material was used in the next step without further purification. mp 177-178° C. $^1$H NMR (DMF-d$_7$): δ0.62 (m, 1H), 1.11 (m, 2H), 1.29 (m, 1H), 1.32 (t, $J_{H-H}$=7.0 Hz, 3H), 3.76 (s, 3H), 4.18 (m, 1H), 4.21 (d, $J_{H-F}$=2.0 Hz, 3H), 4.33 (q, $J_{H-H}$=7.0 Hz, 2H), 7.64 (dd, $J_{H-F}$=10.0 Hz, 8.5 Hz, 1H).

Step 2 (R)-7-[3-(1-amino-1-methyl-ethyl)-pyrrolidin-yl]-1-cyclopropyl-6-fluoro-2-methanesulfonyl-8-methoxy-4-oxo-1,4-dihydro-quinoline-3-carboxylic Acid Ethyl Ester (7)

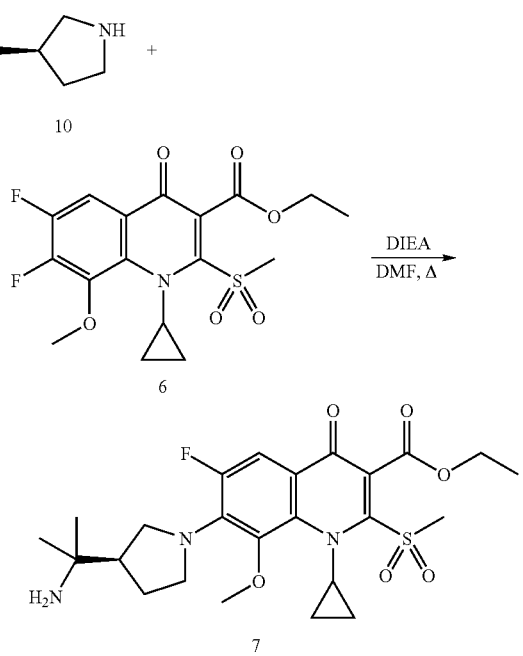

A mixture containing compound (6) (3.88 g, 9.67 mmol), compound 10 (1.64 g, 12.8 mmol), anhydrous DIEA (5.05 g, 39.1 mmol, dried over 4 Å sieves), and anhydrous DMF (40 mL) is heated at 70° C. under an atmosphere of argon gas. After heating for 4.5 h (LC-MS analysis shows ~7% compound (6) remained), the reaction mixture is cooled to room temperature, diluted with EtOAc (200 mL), and washed with water (100 mL). The aqueous layer is extracted with EtOAc (100 mL), and the combined organic layers are washed with a saturated aqueous solution of sodium bicarbonate (100 mL). The organic layer is diluted with water (100 mL) and treated with an aqueous solution of HCl (4 N) until the aqueous layer is acidic (pH 2-3 after shaking the mixture vigorously). The organic layer is separated, and this process is repeated. The combined aqueous layers are diluted with EtOAc (100 mL) and treated with an aqueous solution of sodium hydroxide (6 N) until the aqueous layer is basic (pH ~8 after shaking the mixture vigorously). The aqueous layer is separated, and this process is repeated. The combined organic layers are dried over magnesium sulfate, filtered, and concentrated under reduced pressure giving an orange solid (3.27 g of an ~80:20 mixture of compound (7) and impurity B). This solid is recrystallized from hot EtOAc (~60 mL) furnishing 2.18 g (44% yield) of pure compound 7 as a bright yellow solid. LC-MS m/z calcd for $C_{24}H_{32}FN_3O_6S$ 509 ([M$^+$]); found 510 ([M+H]$^+$).

This reaction should not be allowed to proceed for more than a few hours (not overnight) as prolonged reaction time can lead to the formation of more side products. The product should be ~95% pure (based on HPLC), with only a trace amount of impurity B.

Step. 3. (R)-7-[3-(1-amino-1-methyl-ethyl)-pyrrolidin-yl]-1-cyclopropyl-6-fluoro-2-mercapto-8-methoxy-4-oxo-1,4-dihydro-quinoline-3-carboxylic Acid Ethyl Ester (8)

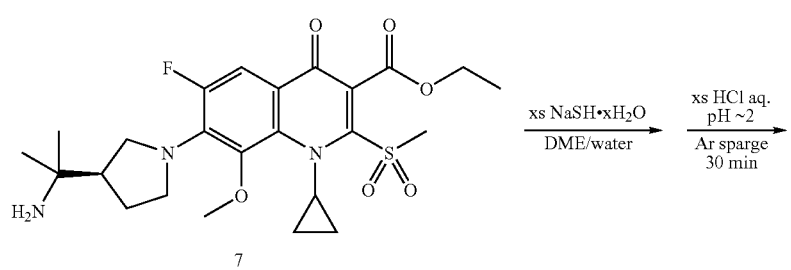

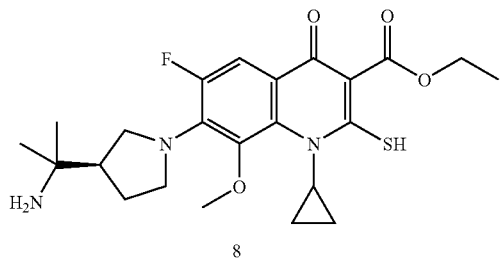

Compound 7 (1.04 g, 2.04 mmol) is partially dissolved in DME (40 mL) under an atmosphere of argon. Sodium hydrosulfide hydrate (Aldrich, 72.6% by titration, 465 mg, 6.02 mmol) in water (3.0 mL) is added to this solution. The resulting mixture is sparged slowly with argon for 30 min. The progress of the reaction is monitored by HPLC-MS, and judged to be complete (≦2% of 7 remains) after 11.5 h. Excess sodium hydrosulfide is quenched upon addition of aq HCl (4.5 mL, 4 N). The resulting orange solution (pH ~2) is sparged with argon (30 min) to remove the generated hydrogen sulfide.

Step. 4 (R)-7-[3-(1-amino-1-methyl-ethyl)-pyrrolidin-1-yl]-9-cyclopropyl-6-fluoro-8-methoxy-9H-isothiazolo[5,4-b]-quinoline-3,4-dione (5)

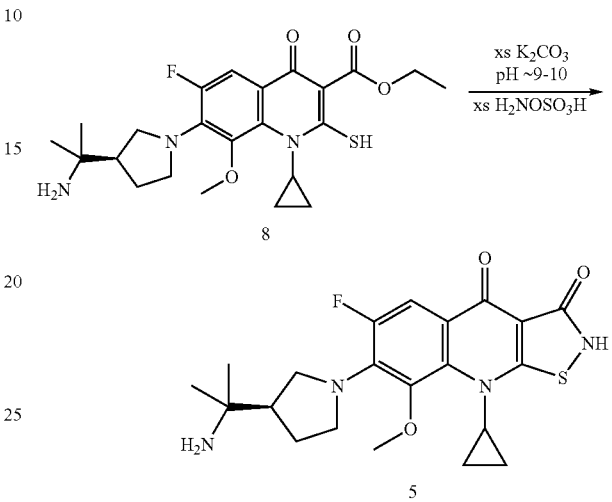

A solution of potassium carbonate (4.26 g, 30.8 mmol) in water (25 mL) is next added to this solution to give a clear yellow solution (pH 9-10). The clear yellow solution is then sparged with argon for ~5 min. Finally, hydroxylamine-O-sulfonic acid (0.93 g, 8.2 mmol) is added portionwise as a solid, with immediate evolution of gas and formation of the product as a yellow precipitate. After stirring for 16 h, the reaction mixture (pH 10.2) is acidified with aq HCl to pH 8.3

Example 2

SYNTHESIS OF (R)-7-[3-(2-AMINOPROPAN-2-YL)PYRROLIDIN-1-YL]-9-CYCLOPROPYL-8-(DIFLUOROMETHOXY)-6-FLUOROUISOTHIA-ZOLO[5,4-B]QUINOLINE3,(2H,9H)-DIONE (11)

Step 1. Ethyl 1-cyclopropyl-8-(difluoromethoxy)-6,7-difluoro-2-methanesulfonyl-4-oxo-1,4-dihydro-quinoline-3-carboxylate (12)

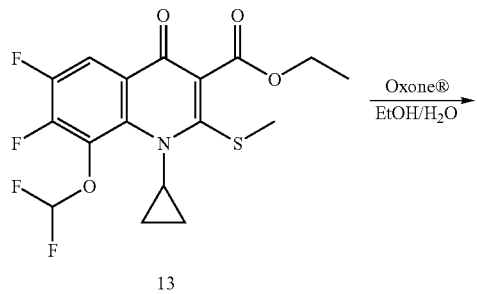

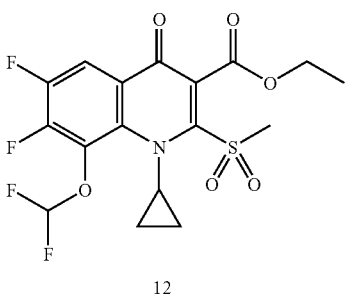

Water (510 mL), followed by OXONE (Dupont Specialty Chemicals) (170 g, 277 mmol), is added to a suspension of 13 (23 g) in EtOH (510 mL). The reaction mixture is heated with stirring at 55-60° C. overnight. The reaction mixture is cooled to room temperature, EtOH is removed under reduced pressure, diluted with water (40 mL), and extracted with EtOAc. The organic layer is dried ($Na_2SO_4$), concentrated and purified to get (40% EtOAc in Hexanes) 13.8 g of sulfone 2 as white solid. $^1$H-NMR ($CDCl_3$): δ 0.39-0.46 (1H, m), 0.85-0.93 (1H, m), 1.09-1.14 (1H, m), 1.24-1.29 (1H, m), 1.38 (3H, t, J=6.0 Hz), 3.47 (3H, s), 4.12-4.19 (1H, m), 4.37-4.48 (2H, m), 6.66 (1H, td, J=72 Hz, 0.9 Hz), 7.91 (1H, dd, J=12 Hz, 9 Hz); $^{19}$F: δ −137.9 (1F, d, J=22.5 Hz), −134.1 (1F, d, J=19.7 Hz), −82.1 (2F, d, J=8.5 Hz); LRMS calc. for $C_{17}H_{15}F_4NO_6S$ 437, found 438 (M+1).

Step 2. (R)-7-[3-(1-amino-1-methyl-ethyl)-pyrrolidin-yl]-1-cyclopropyl-6-fluoro-2-methanesulfonyl-8 (difluor-methoxy)-4-oxo-1,4-dihydro-quinoline-3-carboxylic Acid Ethyl Ester (14)

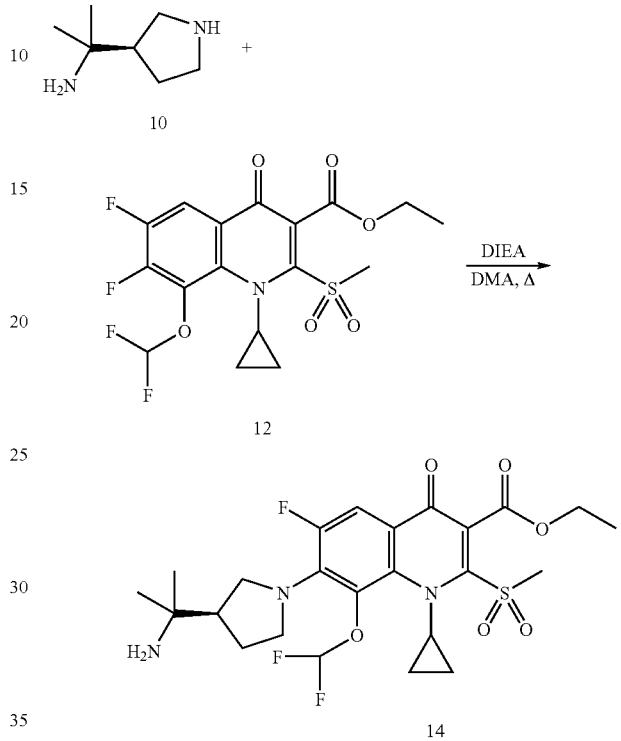

A mixture containing compound (12) (3.0 g, 6.86 mmol), compound (10) (1.32 g, 10.3 mmol), anhydrous DIEA (6.03 ml, 34.3 mmol, dried over 4 Å sieves), and anhydrous N,N-dimethyl acetamide (DMA) (40 mL) is heated at 80° C. under an atmosphere of argon gas. After heating for 1 h, the reaction mixture is cooled to room temperature, diluted with EtOAc (200 mL), and washed with water (100 mL). The aqueous layer is extracted with EtOAc (100 mL), and the combined organic layers are washed with a saturated aqueous solution of sodium bicarbonate (100 mL). The organic layer is diluted with water (100 mL) and treated with an aqueous solution of HCl (4 N) until the aqueous layer is acidic (pH 2-3 after shaking the mixture vigorously). The organic layer is separated, and this process is repeated. The combined aqueous layers are diluted with EtOAc (100 mL) and treated with an aqueous solution of sodium hydroxide (6 N) until the aqueous layer is basic (pH ~8 after shaking the mixture vigorously). The aqueous layer is separated, and this process is repeated. The combined organic layers are dried over magnesium sulfate, filtered, and concentrated under reduced pressure giving an orange solid (4.8 g). $^1$H-NMR ($CDCl_3$): δ 0.36-0.41 (1H, m), 0.83-0.88 (1H, m), 0.98-1.03 (1H, m), 1.19 (6H, d, J=1.8 Hz), 1.18-1.26 (1H, m), 1.38 (3H, t, J=6.0 Hz), 1.71-1.78 (1H, m), 1.98-2.03 (1H, m), 2.22-2.34 (1H, m), 3.36-3.50 (2H, m), 3.43 (3H, s), 3.82-3.91 (1H, m), 4.02-4.13 (2H, m), 4.36-4.47 (2H, m), 6.19 (1H, t, J=75 Hz), 7.62 (1H, d, J=13.8 Hz); $^{19}$F: δ −121.3, −82.9 (d, J=39.5 Hz); LRMS calc. for $C_{24}H_{30}F_3N_3O_6S$ 545, found 546 (M+1).

Step 3. (R)-7-[3-(1-amino-1-methyl-ethyl)-pyrrolidin-yl]-1-cyclopropyl-6-fluoro-2-mercapto-8-(difluoro-methoxy)-4-oxo-1,4-dihydro-quinoline-3-carboxylic Acid Ethyl Ester (15)

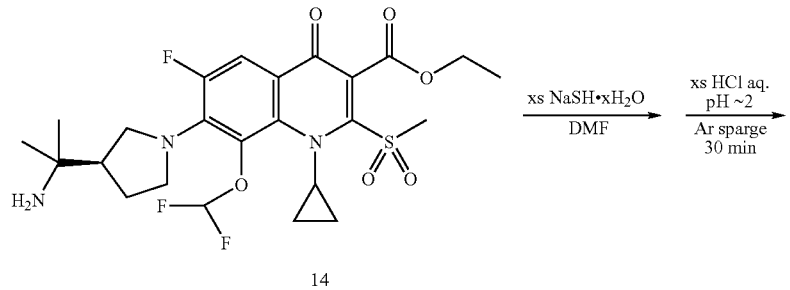

Compound 14 (1.6 g, 2.93 mmol) is dissolved in DMF (40 mL) under an atmosphere of argon. Sodium hydrosulfide hydrate crystals (Aldrich, 72.6% by titration, 330 mg, 5.88 mmol) are added to this solution. The resulting mixture is sparged slowly with argon for 30 min. The progress of the reaction is monitored by HPLC-MS, and judged to be complete (≦2% of 14 remains) after 5 h. Excess sodium hydrosulfide is quenched upon addition of aq. HCl (4.5 mL, 4 N). The resulting orange solution (pH ~2) is sparged with argon (30 min) to remove the generated hydrogen sulfide. DMF is removed under reduced pressure to give orange oil.

Step. 4 (R)-7-[3-(1-amino-1-methyl-ethyl)-pyrrolidin-1-yl]-9-cyclopropyl-6-fluoro-8-(difluoromethoxy)-9H-isothiazolo[5,4-b]-quinoline-3,4-dione (16)

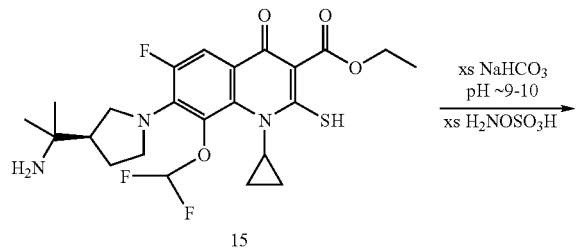

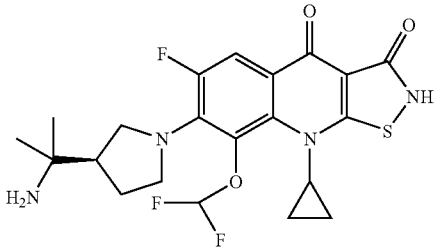

The above oil is taken in THF (30 ml) and 30 ml of water. Solid sodium bicarbonate is added till the pH is 9-10. This heterogeneous solution is then sparged with argon for ~5 min. Finally, hydroxylamine-O-sulfonic acid (1.33 g, 11.7 mmol) is added portion-wise as a solid, with immediate evolution of gas and formation of the product as a yellow precipitate. After stirring for 16 h, the reaction mixture is concentrated to remove THF. Orange solid separates. The reaction mixture was centrifuged and the supernatant is decanted. The product along with solid sodium bicarbonate is washed with water (3×40 mL, with sonication), and lyophilized to give 0.75 g of 16. $^1$H-NMR (TFA-D): δ 1.19-1.33 (2H, m), 1.45-1.57 (2H, m), 1.58 (6H, s), 1.95-2.05 (1H, m), 2.27-2.36 (1H, m), 2.78-2.88 (1H, m), 3.81-4.23 (5H, m), 6.41 (1H, t, J=72 Hz), 7.98 (1H, d, J=12.9 Hz); $^{19}$F (DMSO-D$_6$): δ −124.9, −84.4 (d, J=42.3 Hz); LRMS calc. for $C_{21}H_{23}F_3N_4O_3S$ 468, found 469 (M+1).

Example 3

SYNTHESIS OF 7-((R)-3-((S)-1-AMINOETHYL)PYRROLIDIN-1-YL)-9-CYCLOPROPYL-6-FLUORO-8-METHOXYISOTHIAZOLO[5,4-B]QUINOLINE-3,4(2H,9H)-DIONE (17)

Step 1. Ethyl 7-((R)-3-((S)-1-aminoethyl)pyrrolidin-1-yl)-1-cyclopropyl-6-fluoro-8-methoxy-2-(methylsulfonyl)-4-oxo-1,4-dihydroquinoline-3-carboxylate (18)

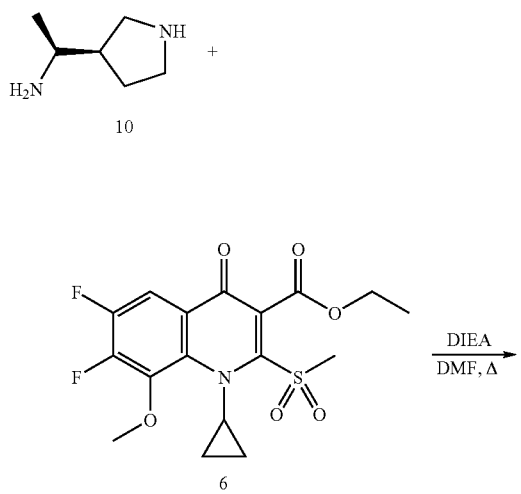

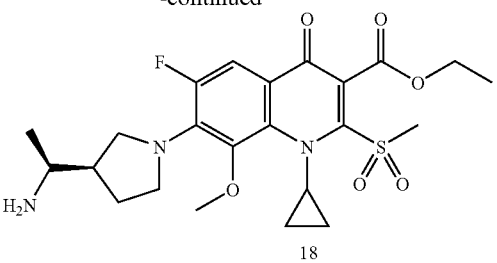

A mixture containing compound (6) (16.7 g, 41.6 mmol), compound (10) (5.58 g, 48.9 mmol), anhydrous DIEA (20.8 g, 161 mmol, dried over 4 Å sieves), and anhydrous DMF (128 mL) is heated at 70° C. under an atmosphere of argon gas. After heating for 6 h (LC-MS analysis shows ~7% compound (6) remained), the reaction mixture is cooled to room temperature, diluted with EtOAc (500 mL), and washed with water (500 mL). The aqueous layer is extracted with EtOAc (500 mL), and the combined organic layers are washed with a saturated aqueous solution of sodium bicarbonate (500 mL). The organic layer is diluted with water (500 mL) and treated with an aqueous solution of HCl (4 N) until the aqueous layer is acidic (pH 2-3 after shaking the mixture vigorously). The organic layer is separated, and this process is repeated. The combined aqueous layers are diluted with EtOAc (500 mL) and treated with an aqueous solution of sodium hydroxide (6 N) until the aqueous layer is basic (pH ~8 after shaking the mixture vigorously). The aqueous layer is separated, and this process is repeated. The combined organic layers are dried over magnesium sulfate, filtered, and concentrated under reduced pressure giving an orange solid. Crude solid is used directly to next reaction.

Step 2. Ethyl 7-((R)-3-((S)-1-aminoethyl)pyrrolidin-1-yl)-1-cyclopropyl-6-fluoro-2-mercapto-8-methoxy-4-oxo-1,4-dihydroquinoline-3-carboxylate (19)

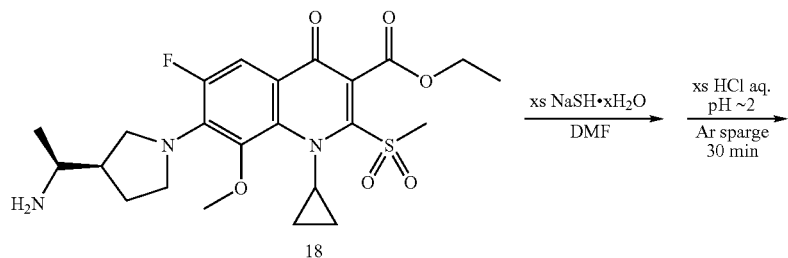

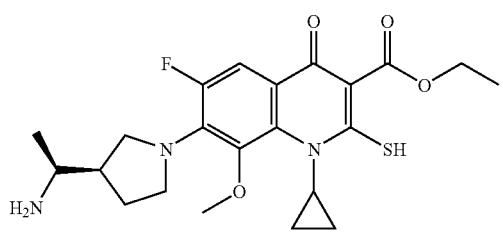

Compound 18 from previous reaction is partially dissolved in DME (150 mL) under an atmosphere of argon. Sodium hydrosulfide hydrate (Aldrich, 72.6% by titration, 4.65 g, 60.2 mmol) in water (15.0 mL) is added to this solution. The resulting mixture is sparged slowly with argon for 30 min. The progress of the reaction is monitored by HPLC-MS, and judged to be complete (≦2% of 18 remains) after 15 h. Excess sodium hydrosulfide is quenched upon addition of aq HCl (30 mL, 6 N). The resulting orange solution (pH ~2) is sparged with argon (3 h) to remove the generated hydrogen sulfide.

Step 3. 7-((R)-3-((S)-1-aminoethyl)pyrrolidin-1-yl)-9-cyclopropyl-6-fluoro-8-methoxyisothiazolo[5,4-b] quinoline-3,4(2H,9H)-dione (19)

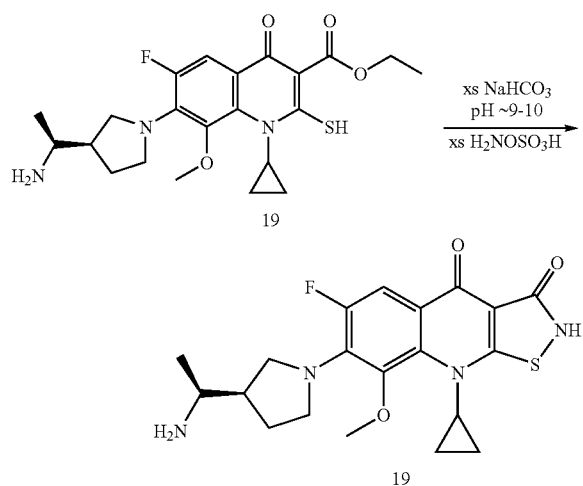

A solution of potassium carbonate (30 g, 217 mmol) in water (150 mL) is next added to this solution to give a clear yellow solution (pH 9-10). The clear yellow solution is then sparged with argon for 5 min. Finally, hydroxylamine-O-sulfonic acid (93 g, 82 mmol) is added portionwise as a solid, with immediate evolution of gas and formation of the product as a yellow precipitate. After stirring for 15 h, the reaction mixture (pH 10.2) is acidified with aq HCl to pH 8.3 (the approximate isoelectric point of 20) causing additional product to precipitate from solution. The reaction mixture is concentrated under reduced pressure (final volume 40 mL). The yellow precipitate is collected by centrifugation, washed with water (3×40 mL, with sonication), and lyophilized to give 7.3 g of 20. LC-MS m/z calcd for $C_{20}H_{23}FN_4O_3S$ 418 ([M+]); found 419 ([M+H]+). $^1$H NMR (DMSO-$d_6$) δ 8.15 (br, 3H), 7.55 (d, $J_{H,F}$=13.9 Hz 1H), 3.86-3.51 (m, 3H), 3.52 (s, 3H, methoxy), 3.51-3.45 (m, 2H), 3.29 (m, 1H), 2.42 (m, 1H), 2.09 (m, 1H), 1.75 (m, 1H), 1.29 (d, J=6.5 Hz, 3H, methyl), 1.14 (m, 2H, c-Pr), 0.95 (m, 2H, c-Pr). $^{19}$F NMR (DMSO-$d_6$) δ −125.4 (s, 1F).

What is claimed is:

1. A compound of the formula:

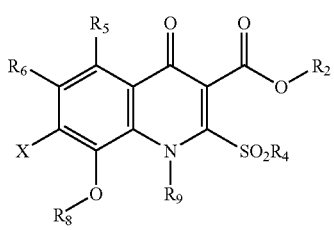

wherein
$R_2$ is $C_1$-$C_6$alkyl, $C_2$-$C_6$alkenyl, $(C_3$-$C_7$cycloalkyl)$C_0$-$C_4$alkyl, (aryl)$C_0$-$C_4$alkyl, or $(C_2$-$C_6$heterocycloalkyl)$C_0$-$C_2$alkyl, each of which is substituted with 0 to 5 substituents independently chosen from halogen, hydroxy, amino, cyano, nitro, $C_1$-$C_4$alkyl, $C_1$-$C_4$alkoxy, $C_1$-$C_2$haloalkyl, $C_1$-$C_2$haloalkoxy, mono- and di-$C_1$-$C_4$alkylamino, $C_2$-$C_4$alkanoyl, and $C_1$-$C_4$alkylthio;

$R_4$ is $C_1$-$C_6$alkyl, $C_2$-$C_6$alkenyl, $(C_3$-$C_7$cycloalkyl)$C_0$-$C_4$alkyl, (aryl)$C_0$-$C_4$alkyl, or $(C_2$-$C_6$heterocycloalkyl)$C_0$-$C_2$alkyl, each of which is substituted with 0 to 5 substituents independently chosen from halogen, hydroxy, amino, cyano, nitro, $C_1$-$C_4$alkyl, $C_1$-$C_4$alkoxy, $C_1$-$C_2$haloalkyl, $C_1$-$C_2$haloalkoxy, mono- and di-$C_1$-$C_4$alkylamino, $C_2$-$C_4$alkanoyl, and $C_1$-$C_4$alkylthio;

$R_5$ is hydrogen, hydroxy, amino, $C_1$-$C_2$alkyl, $C_1$-$C_2$alkoxy, mono- or di-$(C_1$-$C_4$alkyl)amino, or mono- or di-$C_1$-$C_4$alkylhydrazinyl;

$R_6$ is hydrogen, halogen, or amino;

X is chloro, bromo, fluoro; iodo, or triflate;

$R_8$ is $C_1$-$C_6$alkyl, $C_1$-$C_2$haloalkyl, or $C_3$-$C_7$cycloalkyl substituted with 0 or 1 or more halogen atoms; and $R_9$ is $C_1$-$C_4$alkyl, cyclopropyl, or phenyl, each of which is substituted with 0 to 3 substituents independently chosen from halogen, hydroxy, amino, $C_1$-$C_2$alkyl, $C_1$-$C_2$alkoxy, mono- and di-$(C_1$-$C_2)$alkylamino, $C_1$-$C_2$haloalkyl, and $C_1$-$C_2$haloalkoxy.

2. A compound of claim 1, wherein $R_2$ is $C_1$-$C_4$alkyl.

3. A compound of claim 1, wherein $R_2$ is ethyl.

4. A compound of claim 1, wherein $R_4$ is $C_1$-$C_4$alkyl.

5. A compound of claim 4, wherein $R_4$ is methyl.

6. A compound of claim 1, wherein $R_2$ is ethyl and $R_4$ is methyl.

7. A compound of claim 1, wherein $R_5$ is hydrogen.

8. A compound of claim 1, wherein $R_6$ is fluoro or hydrogen.

9. A compound of claim 8, wherein $R_6$ is fluoro.

10. A compound of claim 1, wherein
$R_8$ is methoxy; and
$R_9$ is $C_1$-$C_4$alkyl or cyclopropyl, or
$R_9$ is phenyl substituted with 2 substituents chosen from halogen, hydroxy, amino, $C_1$-$C_2$alkyl, $C_1$-$C_2$alkoxy, mono- and di-$(C_1$-$C_2)$alkylamino, $C_1$-$C_2$haloalkyl, and $C_1$-$C_2$haloalkoxy.

11. A compound of claim 10, wherein $R_9$ is cyclopropyl.

12. A process for the preparation of a compound of claim 1, comprising oxidizing a compound of the formula

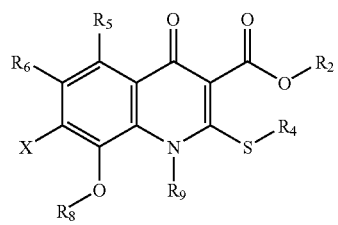

with an oxidizing agent to produce a compound of claim 1.

13. The process of claim 12, wherein the oxidizing agent is potassium monoperoxysulfate, urea hydrogen peroxide, meta-chloroperbenzoic acid, UHP, sodium periodate, or a mixture of any of the foregoing.

* * * * *